United States Patent
Zellner et al.

(10) Patent No.: US 10,190,520 B1
(45) Date of Patent: Jan. 29, 2019

(54) SIGNAL CONDITIONING MODULE FOR A WIDE-BAND OXYGEN SENSOR

(71) Applicant: Harley-Davidson Motor Company Group, LLC, Milwaukee, WI (US)

(72) Inventors: Charles Zellner, Menomonee Falls, WI (US); Scott A. Koerner, Allenton, WI (US); Thomas Carl, Hartford, WI (US)

(73) Assignee: Harley-Davidson Motor Company Group, LLC, Milwaukee, WI (US)

( * ) Notice: Subject to any disclaimer, the term of this patent is extended or adjusted under 35 U.S.C. 154(b) by 0 days.

(21) Appl. No.: 15/730,903

(22) Filed: Oct. 12, 2017

(51) Int. Cl.
*F02D 41/14* (2006.01)
*G01N 33/00* (2006.01)
*F02D 41/00* (2006.01)

(52) U.S. Cl.
CPC ..... *F02D 41/1479* (2013.01); *F02D 41/0042* (2013.01); *F02D 41/14* (2013.01); *F02D 41/1438* (2013.01); *F02D 41/1454* (2013.01); *G01N 33/004* (2013.01); *G01N 33/0009* (2013.01); *G01N 33/0011* (2013.01)

(58) Field of Classification Search
CPC .. F02D 41/1454; F02D 41/1438; F02D 41/14; F02D 41/1479; G01N 33/0009; G01N 33/0011; G01N 33/004
USPC ........... 123/704; 701/109; 60/276; 73/23.31
See application file for complete search history.

(56) References Cited

U.S. PATENT DOCUMENTS

| | | | | |
|---|---|---|---|---|
| 4,130,095 A | * | 12/1978 | Bowler | F02D 41/2454 |
| | | | | 123/675 |
| 4,245,314 A | * | 1/1981 | Henrich | F02P 5/1502 |
| | | | | 123/453 |
| 4,844,788 A | | 7/1989 | Takahashi et al. | |
| 5,065,579 A | * | 11/1991 | Monahan | F02G 1/045 |
| | | | | 60/524 |

(Continued)

FOREIGN PATENT DOCUMENTS

DE    10016886 A1    10/2001

OTHER PUBLICATIONS

Dynojet, Wide Band 2 Installation Guide, www.dynojetwb2.com, Part No. 98200017 Version 03 (Oct. 2008).

(Continued)

*Primary Examiner* — Mahmoud Gimie
(74) *Attorney, Agent, or Firm* — Michael Best & Friedrich LLP

(57) ABSTRACT

A signal conditioning module for a wide-band oxygen sensor and methods of installing the same. One signal conditioning module includes an electronic processor, a first electrical coupling, and a second electrical coupling. The first coupling is configured to be coupled to a port of an electrical harness. The power is configured to receive an electrical coupling of a narrow-band oxygen sensor signal for providing power to the narrow-band oxygen sensor. The second coupling is configured to be coupled to the wide-band oxygen sensor. The electronic processor receives power over the first coupling, powers the wide-band oxygen sensor over the second coupling using the received power, (Continued)

receives first data over the second coupling from the wideband oxygen sensor, converts the first data to second data, and outputs the second data over the first coupling to the electrical harness for transmission to an electronic control unit coupled to the electrical harness.

19 Claims, 6 Drawing Sheets

(56) References Cited

U.S. PATENT DOCUMENTS

| | | | |
|---|---|---|---|
| 5,259,358 A * | 11/1993 | Chen | F01N 3/2053 123/697 |
| 5,291,673 A | 3/1994 | Hamburg et al. | |
| 5,345,921 A | 9/1994 | Iwano et al. | |
| 5,970,968 A | 10/1999 | Davis | |
| 6,371,096 B1 | 4/2002 | Ohsaki et al. | |
| 6,672,900 B2 | 1/2004 | France et al. | |
| 6,681,752 B1 | 1/2004 | Kreikemeier et al. | |
| 6,854,262 B2 | 2/2005 | Yoshizawa et al. | |
| 7,325,393 B2 | 2/2008 | Miura | |
| 7,359,789 B2 | 4/2008 | Hackel et al. | |
| 7,455,058 B2 | 11/2008 | Raffesberger | |
| 7,665,444 B2 | 2/2010 | Marin et al. | |
| 7,832,196 B2 | 11/2010 | Westerbeke, Jr. | |
| 7,926,330 B2 | 4/2011 | Huang et al. | |
| 7,945,373 B2 | 5/2011 | Vestrini et al. | |
| 8,082,892 B2 | 12/2011 | Zhou et al. | |
| 8,121,744 B2 | 2/2012 | Sell et al. | |
| 8,135,508 B1 | 3/2012 | Thompson et al. | |
| 8,484,956 B2 | 7/2013 | Mastbergen | |
| 8,551,664 B2 | 10/2013 | Tighe et al. | |
| 8,670,917 B2 | 3/2014 | Aoki et al. | |
| 8,720,416 B2 | 5/2014 | Amann et al. | |
| 8,815,188 B2 | 8/2014 | Yacoub et al. | |
| 8,939,010 B2 | 1/2015 | Levijoki et al. | |
| 8,996,279 B2 | 3/2015 | Dobeck et al. | |
| 9,133,785 B2 | 9/2015 | Kociba et al. | |
| 9,291,526 B2 | 3/2016 | Fosaaen | |
| 2002/0048991 A1 * | 4/2002 | France | H01R 13/5205 439/587 |
| 2004/0020480 A1 * | 2/2004 | Kreikemeier | F02D 41/1454 123/683 |
| 2007/0068917 A1 * | 3/2007 | Smith | G01N 27/4067 219/237 |
| 2010/0170794 A1 | 7/2010 | Gibson et al. | |
| 2011/0043349 A1 | 2/2011 | Johnson | |
| 2011/0208409 A1 | 8/2011 | Snyder et al. | |
| 2012/0324864 A1 | 12/2012 | Krengel et al. | |
| 2013/0024094 A1 | 1/2013 | Shaver et al. | |
| 2013/0231846 A1 | 9/2013 | Magner et al. | |
| 2014/0060506 A1 | 3/2014 | Shaver | |
| 2014/0309908 A1 | 10/2014 | Vosburg | |
| 2015/0033757 A1 | 2/2015 | White et al. | |
| 2015/0152791 A1 | 6/2015 | White | |
| 2015/0354485 A1 | 12/2015 | Santillo et al. | |
| 2016/0266062 A1 * | 9/2016 | Nishijima | G01N 27/419 |

OTHER PUBLICATIONS

Dynojet, Wide Band 2 Product Details, http://www.dynojetwb2.com/wb2_details.aspx, webpage available at least as early as Feb. 6, 2017.

Lamda Sensor LSU 4.9 Datasheet, www.bosch-motorsport.com, V3, 28, Sep. 2015.

Milot, "Steady-State Wide-Range Air-Fuel Ratio Control 922172", Downloaded from SAE International by Cari Brown, Tuesday, Apr. 12, 2016.

Y Chung, et al., "A new concept of misfire detection using a wide-range oxygen sensor in a spark-ignition engine", Proc Instn Mech Engrs vol. 213 Part D IMechE 1999.

Kainz, et al. "Individual Cylinder Fuel Control with a Switching Oxygen Sensor", International Congress and Exposition Detroit, MI Mar. 1-4, 1999, 1999-01-0546.

Powell, et al., "Observer-Based Air-Fuel Ratio Control", Oct. 1998, pp. 72-83.

Maloney, "A Production Wide-Range AFR Sensor Response Diagnostic Algorithm for Direct-Injection Gasoline Application 2001-01-0558", Downloaded from SAE International by Cari Brown, Thursday, Apr. 14, 2016.

Inagaki et al., An adaptive Fuel Injection Control with Internal Model in Automotive Engines, IEEE 1990, pages.

* cited by examiner

SIGNAL CONDITIONING MODULE FOR A WIDE-BAND OXYGEN SENSOR

FIELD

Embodiments described herein relate to a signal conditioning module for a wide-band oxygen sensor and methods for installing the same.

SUMMARY

An oxygen sensor (also sometimes referred to as a lambda sensor) is an electronic device that measures a proportion of oxygen (O2) in a gas or liquid. Vehicles commonly include one or more oxygen sensors to measure an amount of oxygen in exhaust exiting the vehicle's internal combustion engine. The amount of oxygen is used to determine an air-to-fuel ratio of the engine. A vehicle or a fuel may be associated with a desired air-to-fuel ratio that is referred to as a stoichiometric ratio. For example, gasoline typically has a stoichiometric ratio of 14.7:1. When a determined air-to-fuel ratio differs from the stoichiometric ratio, the air-to-fuel ratio is considered "rich" (too much fuel) or "lean" (too little fuel). Thus, fuel injection systems may use a determined air-to-fuel ratio to dynamically adjust an amount of fuel injected into the engine to compensate for excess air or excess fuel.

Narrow-band oxygen sensors provide a binary output representing whether the air-to-fuel ratio is rich or lean. For example, a narrow-band oxygen sensor may output a voltage of 0.2 V (200 mV) DC to represent a lean ratio and may output a voltage of 0.8 V (800 mV) DC to represent a rich ratio. In contrast, wide-band oxygen sensors provide an analog output representing an actual air-to-fuel ratio. Accordingly, a vehicle system receiving output from a wide-band oxygen sensor can better manage fuel consumption than a vehicle system receiving output from a narrow-band oxygen sensor. In general, however, narrow-band oxygen sensors cannot simply be replaced with wide-band oxygen sensors. In particular, the two different types of sensors provide output at different voltages. Thus, vehicle hardware, such as an electronic control unit, may not be configured to accept the range of voltages output by a wide-band oxygen sensor.

Accordingly, embodiments described herein provide a signal conditioning module for wide-band oxygen sensors and methods for installing the same. For example, one embodiment provides a signal conditioning module for a wide-band oxygen sensor installed in a vehicle. The signal conditioning module includes an electronic processor, a first electrical coupling, and a second electrical coupling. The first electrical coupling is configured to be coupled to a port of an electrical harness. The port is configured to receive an electrical coupling of a narrow-band oxygen sensor signal for providing power to the narrow-band oxygen sensor. The second electrical coupling configured to be coupled to the wide-band oxygen sensor. The electronic processor receives power over the first electrical coupling, powers the wide-band oxygen sensor over the second electrical coupling using the power received over the first electrical coupling, receives first data over the second electrical coupling from the wide-band oxygen sensor, converts the first data to second data, and outputs the second data over the first electrical coupling to the electrical harness for transmission to an electronic control unit coupled to the electrical harness.

Another embodiment provides a method of installing a signal conditioning module for a wide-band oxygen sensor. The method includes coupling a first electrical coupling of the signal conditioning module to a port of an electrical harness configured to be coupled to a narrow-band oxygen sensor, and coupling a second electrical coupling of the signal conditioning module to the wide-band oxygen sensor. The signal conditioning module receives power over the first electrical coupling, powers the wide-band oxygen sensor over the second electrical coupling using the power received over the first electrical coupling, receives first data from the second electrical coupling from the wide-band oxygen sensor, converting the first data to second data, and outputs the second data over the first electrical coupling to the electrical harness for transmission to an electronic control unit coupled to the electrical harness.

Yet another embodiment a system for installing a wide-band oxygen sensor in a vehicle. The system includes the wide-band oxygen sensor, an electrical harness, and a signal conditioning module. The electrical harness is coupled to a power source included in the vehicle and includes a port configured to be coupled to a narrow-band oxygen sensor for providing power to the narrow-band oxygen sensor and receiving data from the narrow-band oxygen sensor. The signal conditioning module includes a first electrical coupling configured to be coupled to the port of the electrical harness and a second electrical coupling configured to be coupled to the wide-band oxygen sensor. The signal conditioning module receives power over the first electrical coupling, powers the wide-band oxygen sensor over the second electrical coupling using the power received over the first electrical coupling, receives first data over the second electrical coupling from the wide-band oxygen sensor, converts the first data to second data, and outputs the second data over the first electrical coupling to the electrical harness for transmission to an electronic control unit coupled to the electrical harness.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect. The term "predetermined" means specified prior to an event. In addition, electronic communications and notifications may be performed using wired connections, wireless connections, or a combination thereof and may be transmitted directly or through one or more intermediary devices over various types of networks, communication channels, and connections. Moreover, relational terms such as first and second, top and bottom, and the like may be used herein solely to distinguish one entity or action from another entity or action without necessarily requiring or implying any actual such relationship or order between such entities or actions.

Figure 1:
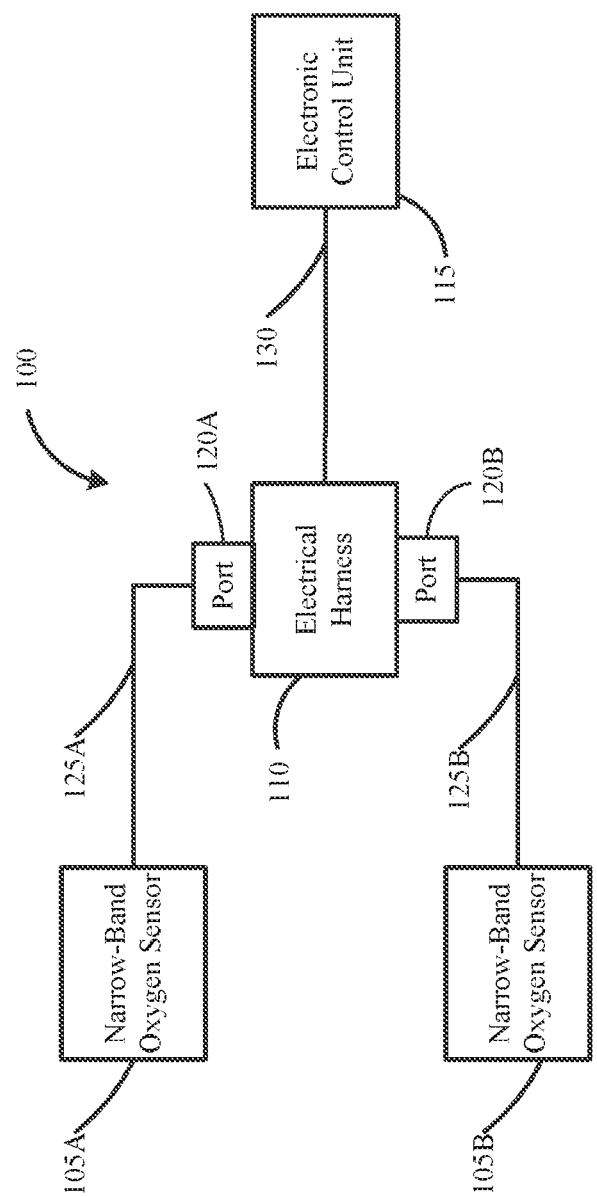
FIG. 1 schematically illustrates a vehicle system including narrow-band oxygen sensors.

As described above, a vehicle includes one or more oxygen sensors to detect an air-to-fuel ratio. For example, FIG. 1 illustrates a vehicle system 100. The system 100 includes two narrow-band oxygen sensors 105A, 105B, an electrical harness 110, and an electronic control unit (ECU) 115. The electrical harness 110 is coupled to a power source (not shown). For example, the electrical harness 110 may be coupled to an electrical system included in the vehicle, a battery, or a combination thereof.

As also described above, each narrow-band oxygen sensor 105A and 105B is configured to output voltages within one of two distinct voltage ranges depending on whether the air-to-fuel ratio is rich or lean. Each narrow-band oxygen sensor 105A, 105B is communicatively coupled to the electrical harness 110. Each narrow-band oxygen sensor 105A, 105B may be communicatively coupled to the electrical harness 110 via a dedicated wire, a set of dedicated wires included in an electrical coupling, a communication bus, a wireless connection, and the like.

For example, as illustrated in FIG. 1, the electrical harness 110 may include a first port 120A for receiving an electrical coupling 125A from the narrow-band oxygen sensor 105A and a second port 120B for receiving an electrical coupling 125B from the narrow-band oxygen sensor 105B. In some embodiments, the electrical harness 110 is coupled to more or fewer narrow-band oxygen sensors. Also, in some embodiments, the system 100 includes a separate electrical harness for each narrow-band oxygen sensor 105A, 105B. Each port 120A, 120B may be configured to receive a connector or adapter included at the end of each electrical coupling 125A, 125B. The ports 120A, 120B and the connectors may be coupled using a snap-fit, a friction fit, a locking mechanism, or the like.

The electrical harness 110 receives output voltages from the narrow-band oxygen sensors 105A, 105B and provides power to the narrow-band oxygen sensors 105A, 105B via the electrical couplings 125A, 125B. For example, each electrical coupling 125A, 125B includes one or more wires for receiving a voltage output of the narrow-band oxygen sensor 105A, 105B and one or more wires for providing power to the narrow-band oxygen sensor 105A, 105B. In particular, each narrow-band oxygen sensor 105A, 105B may include a heating element that is heated to a predetermined temperature required for operation of the sensors 105A, 105B. For example, in some embodiments, a heating element heats an oxygen sensor to approximately 316° C. (600° F.).

As illustrated in FIG. 1, the ECU 115 is also communicatively coupled to the electrical harness 110. The ECU 115 may be communicatively coupled to the electrical harness 110 via a dedicated wire, a set of dedicated wires in an electrical coupling, a communication bus, a wireless connection, and the like. For example, as illustrated in FIG. 1, the ECU 115 is communicatively coupled to the electrical harness 110 via an electrical coupling 130. The ECU 115 may be a general purpose microprocessor, an application specific integrated circuit (ASIC), or other suitable electronic device. For example, in one embodiment, the ECU 115 includes an electronic processor, a memory, and a communication interface for communicating with one or more devices or networks external to the ECU 115, such as the electrical harness 110.

In some embodiments, the ECU 115 receives power from the electrical harness 110 via the electrical coupling 130. Alternatively or in addition, the ECU 115 may be coupled to a separate power source. The ECU 115 receives the output voltages from the narrow-band oxygen sensors 105A, 105B through the electrical harness 110 via the electrical coupling 130. The ECU 115 may process the voltages to dynamically adjust vehicle operation. For example, the ECU 115 may be included in a fuel injection system that dynamically adjusts the amount of fuel injected into the engine based on the output voltages from the narrow-band oxygen sensors 105A, 105B. In other embodiments, the ECU 115 may provide the received voltages to another ECU or vehicle system for processing. In some embodiments, the ECU 115 also controls power supplied to the narrow-band oxygen sensors 105A, 105B through the electrical harness 110 for the heater elements.

As described above, wide-band oxygen sensors provide more information regarding the air-to-fuel ratio of a vehicle than a narrow-band oxygen sensor. However, depending on the ECU 115, a narrow-band oxygen sensor cannot be replaced with a wide-band oxygen sensor without also replacing the ECU 115, which increases the cost and complexity of replacing narrow-band oxygen sensors with wide-band oxygen sensors.

To address these and other issues, embodiments described herein provide a signal conditioning module for a wide-band oxygen sensor. As described below in more detail, the signal conditioning module converts data output by one or more wide-band oxygen sensors into a format (a voltage relationship) acceptable and useable by an existing ECU. The signal conditioning module also uses existing power and communication configurations to further decrease the complexity of installing the wide-band oxygen sensors and the signal conditioning module in a vehicle.

Figure 2:
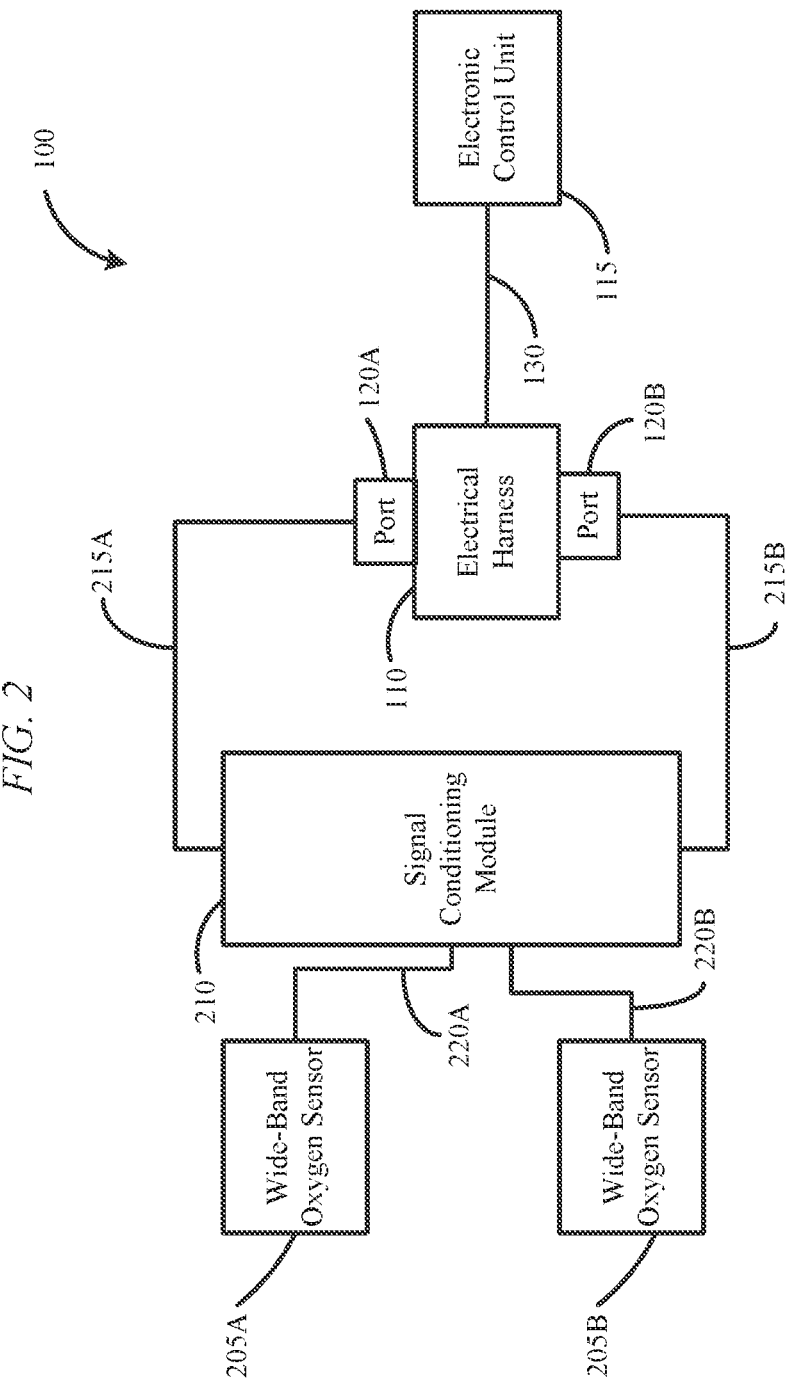
FIG. 2 schematically illustrates the vehicle system of FIG. 1 with the narrow-band oxygen sensors replaced with wide-band oxygen sensors according to one embodiment.

For example, FIG. 2 illustrates the vehicle system 100 with the narrow-band oxygen sensors 105A, 105B replaced with wide-band oxygen sensors 205A, 205B according to one embodiment. As illustrated in FIG. 2, the system 100 also includes a signal conditioning module 210. The signal conditioning module 210 may include similar components as the ECU 115. For example, the signal conditioning module 210 may be a general purpose microprocessor, an application specific integrated circuit (ASIC), or other suitable electronic device that may include an electronic processor, a memory, and a communication interface for communicating with one or more devices or networks external to the signal conditioning module 210. As described in more detail below, the signal conditioning module 210 is configured to measure the pumping current consumed by the wide-band oxygen sensors 205A, 205B and convert the pumping current to a voltage useable by the ECU 115. Thus, the signal conditioning module 210 may act as an intermediary device between the wide-band oxygen sensors 205A, 205B and the ECU 115.

Figure 3:
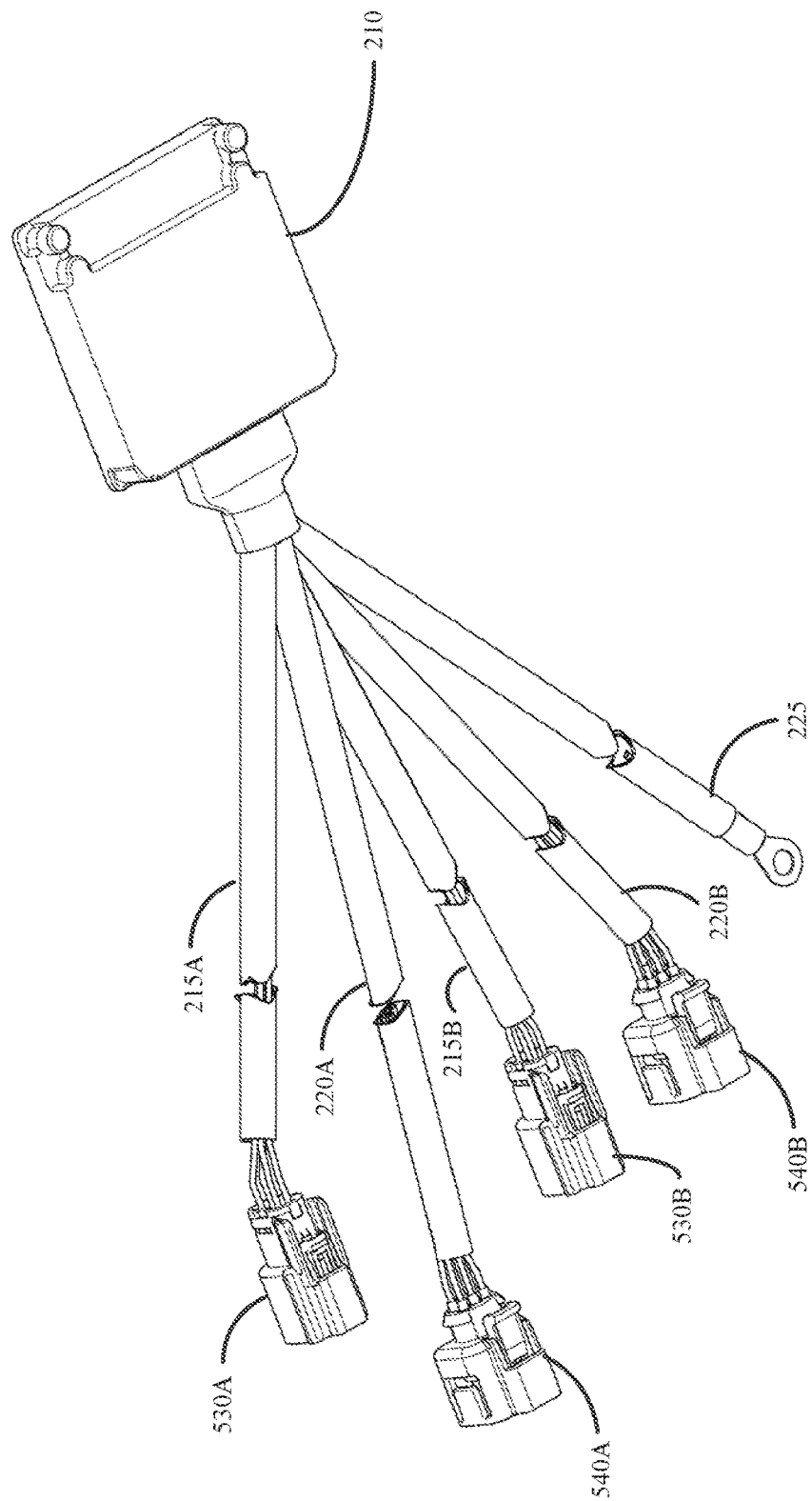
FIG. 3 is a perspective view of a signal conditioning module included in the vehicle system of FIG. 2 according to one embodiment.

FIG. 3 is a perspective view of the signal conditioning module 210 according to one embodiment. The signal conditioning module 210 includes a first electrical coupling 215 configured to be coupled to the electrical harness 110. In particular, the first electrical coupling 215 is configured to be coupled to one of the ports 120A, 120B of the electrical harness 110, which, as described above, are each configured to receive the electrical coupling 125A, 125B from a narrow-band oxygen sensor 105A, 105B. The signal conditioning module 210 also includes a second electrical coupling 220 configured to be coupled to one of the wide-band oxygen sensors 205A, 205B. In some embodiments, the signal conditioning module 210 includes a plurality of first electrical couplings 215, a plurality of second electrical couplings 220, or a combination thereof. For example, as illustrated in FIGS. 2 and 3, in some embodiments, the signal conditioning module 210 includes a first electrical coupling 215 (215A, 215B) and a second electrical coupling 220 (220A, 220B) for each wide-band oxygen sensor 205A, 205B included in the system 100. In some embodiments, as illustrated in FIG. 3, the signal conditioning module 210 also includes a ground wire 225.

Figure 4:
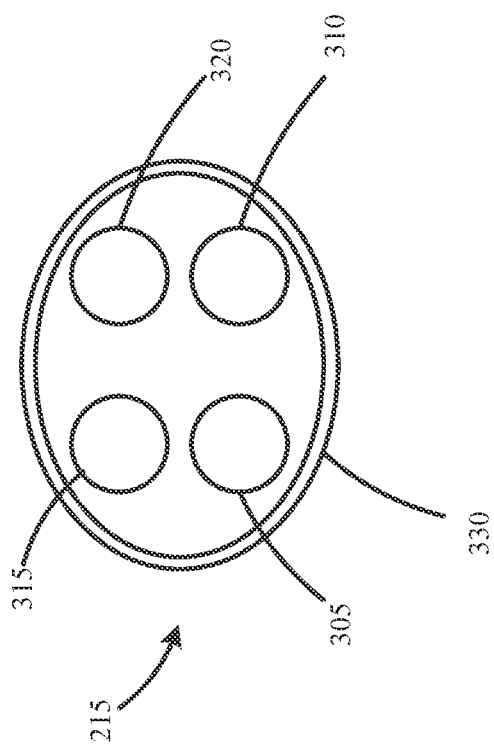
FIG. 4 schematically illustrates an electrical coupling included in the signal conditioning module of FIG. 3 that is coupled to an electrical harness according to one embodiment.

As illustrated in FIG. 4, in one embodiment, the first electrical coupling 215 includes a sensor signal wire 305, a sensor ground wire 310, a heater wire 315, and a heater ground wire 320 within a casing 330. The sensor signal wire 305 transmits data from the signal conditioning module 210, and the sensor ground wire 310 acts as a ground for the sensor signal wire 305. The heater wire 315 transmits power to the signal conditioning module 210, and the heater ground wire 320 acts as a ground for the heater wire 315. The first electrical coupling 215 may, in some embodiments, include more or less wires than described above and may include multiple casings.

Figure 5:
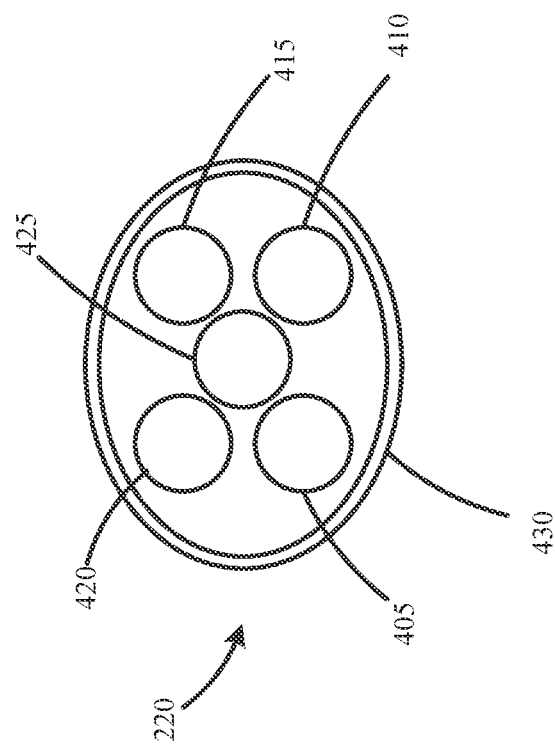
FIG. 5 schematically illustrates an electrical coupling included in the signal conditioning module of FIG. 3 that is coupled to a wide-band oxygen sensor according to one embodiment.

Similarly, as illustrated in FIG. 5, in one embodiment, the second electrical coupling 220 includes sensor signal wires 405 and 425, a sensor ground wire 410, a positive heater wire 415, a negative heater wire 420, and, in some embodiments, a sensor calibration resistor wire (not shown) within a casing 430. The sensor signal wires 405 and 425 transmit data to the signal conditioning module 210, and the sensor ground wire 410 acts as a ground for the sensor signal wires 405 and 425. The positive heater wire 415 transmits power from the signal conditioning module 210, and the negative heater wire 420 acts as a ground for the positive heater wire 415. The sensor ground wire 410 may act as a ground for the entire second electrical coupling 220. The sensor calibration resistor wire may be used by a wide-band oxygen sensor for calibration purposes (e.g., in place of or in addition to performing an air calibration). The second electrical coupling 220 may, in some embodiments, include more or less wires than described above and may include multiple casings.

Figure 6:
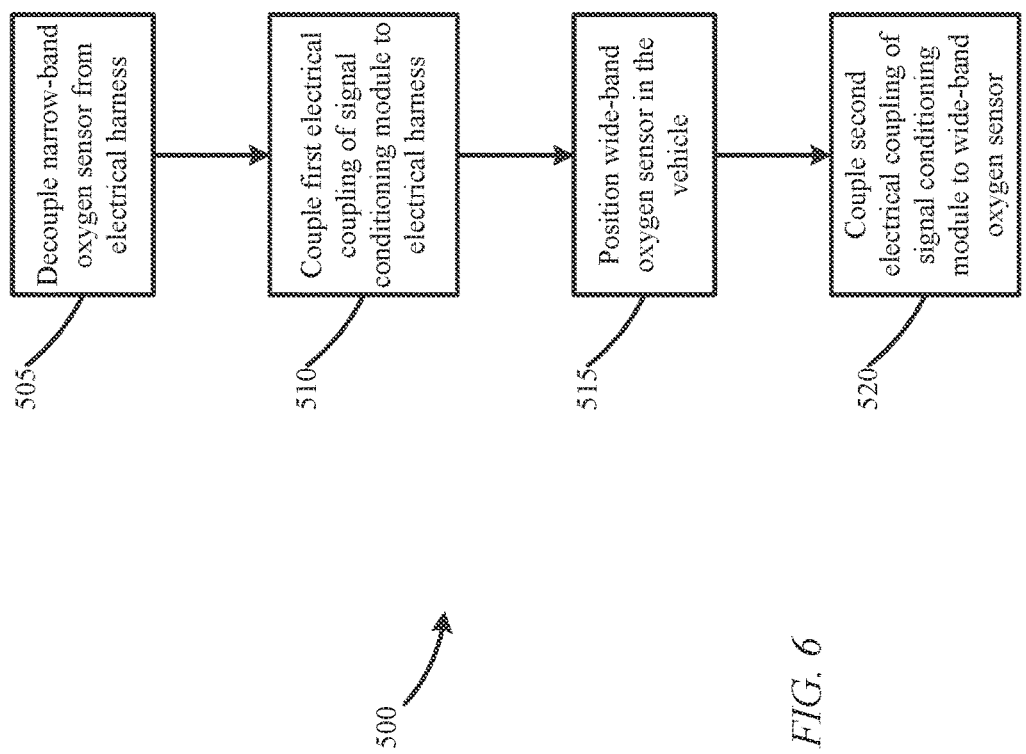
FIG. 6 is a flowchart illustrating method of installing a wide-band oxygen sensor and a signal conditioning module in a vehicle according to one embodiment.

As illustrated in FIG. 2, when installed, the signal conditioning module 210 is coupled between the wide-band oxygen sensors 205A, 205B and the electrical harness 110. For example, FIG. 6 illustrates a method 500 of installing the signal conditioning module 210 illustrated in FIG. 3 according to one embodiment. As illustrated in FIG. 6, when the signal conditioning module 210 is being used with wide-band oxygen sensors 205A, 205B that are replacing existing narrow-band oxygen sensors 105A, 105B, an operator (a person associated with the vehicle such as the owner, driver, maintenance personnel, or the like) decouples the electrical couplings 125A, 125B of the existing narrow-band oxygen sensors 105A, 105B from the electrical harness 110 (at block 505). Decoupling the electrical couplings 125A, 125B may include disconnecting a connector positioned at an end of the electrical couplings 125A, 125B from the ports 120A, 120B. In some embodiments, once decoupled from the electrical harness 110, the narrow-band oxygen sensors 105A, 105B may be removed from the vehicle. However, in other embodiments, the narrow-band oxygen sensors 105A, 105B may remain in the vehicle.

After decoupling the narrow-band oxygen sensors 105A, 105B from the electrical harness 110, the first electrical couplings 215A, 215B of the signal conditioning module 210 are coupled to the electrical harness 110. In particular, the first electrical couplings 215A, 215B are coupled to the ports 120A, 120B of the electrical harness 110 configured to couple to a narrow-band oxygen sensor 105A, 105 (via the electrical coupling 125A, 125B) (at block 510). In some embodiments, as illustrated in FIG. 3, the first electrical couplings 215A, 215B each have a connector 530A, 530B for connecting to one of the ports 120A, 120B. The ports 120A, 120B and the connectors 530A, 530B may be coupled using a snap-fit, a friction fit, a locking mechanism, or the like.

As illustrated in FIG. 6, the method 500 also includes positioning (mounting) the wide-band oxygen sensors 205A, 205B at one or more locations within the vehicle, such as within an exhaust path (at block 515). In some embodiments, the wide-band oxygen sensors 205A, 205B are positioned at approximately the same location as the existing narrow-band oxygen sensors 105A, 105B. In other embodiments, however, the wide-band oxygen sensors 205A, 205B are positioned at a different location than the existing narrow-band oxygen sensors 105A, 105B.

The method 500 also includes coupling the second electrical couplings 220A, 220B of the signal conditioning module 210 to the wide-band oxygen sensors 205A, 205B (at block 520). In some embodiments, as illustrated in FIG. 3, the second electrical couplings 220A, 220B each have a connector 540A, 540B for connecting to a port on the wide-band oxygen sensors 205A, 205B. The connectors 540A, 540B on the second electrical couplings 220A, 220B may be the same or different than the connectors 530A, 530B included in the first electrical couplings 215A, 215B and may couple to the ports on the wide-band oxygen sensors 205A, 205B using a snap-fit, a friction fit, a locking mechanism, or the like. Also, in some embodiments, the second electrical couplings 220 are hardwired to the wide-band oxygen sensors 205A, 205B such that the second electrical couplings 220A, 220B do not need to be coupled to the wide-band oxygen sensors 205A, 205B during installation. The ground wire 225 is also coupled to a ground, such as a ground post on a battery in the vehicle, a chassis ground, or the like.

It is to be understood that functionality described above with respect to the method 500 may be performed in a different order than described above. For example, the operator of the vehicle may position the wide-band oxygen sensors 205A, 205B in the vehicle before decoupling the narrow-band oxygen sensors 105A, 105B from the electrical harness 110. Similarly, the signal conditioning module 210 may be coupled to the wide-band oxygen sensors 205A, 205B before the electrical harness 110, may be coupled in parallel, or may be coupled serially for each wide-band oxygen sensor 205A, 205B. Also, in some embodiments, fewer or more wide-band oxygen sensors 205 may be used. For example, in some embodiments, only a single first electrical coupling 215 and a single second electrical coupling 220 needs to be coupled to the electrical harness 110 and a single wide-band oxygen sensor, respectively, during the installation process.

Once installed, the signal conditioning module 210 (an electronic processor included in the signal conditioning module 210) enables operation of the wide-band oxygen sensors 205A, 205B and communication between the wide-band oxygen sensors 205A, 205B and the ECU 115. In particular, the signal conditioning module 210 receives power from the electrical harness 110 via the positive heater wire 315 included in the first electrical couplings 215A, 215B. The signal conditioning module 210 provides at least a portion of the received power to each of the wide-band oxygen sensors 205A, 205B via the positive heater wire 415 included in the second electrical couplings 220A, 220B. The wide-band oxygen sensors 205A, 205B use the received power to heat a heating element and, optionally, power additional circuitry and components included in the sensors 205A, 205B. The signal conditioning module 210 also uses a portion of the received power to power internal circuitry and components of the signal conditioning module 210, such as a microprocessor. In some embodiments, to provide sufficient power to the signal conditioning module 210, the duty cycle of the heater wire 315 is increased to provide voltage from the electrical harness 110 to the signal conditioning module 210 (over each or either first electrical coupling 215A, 215B). For example, in some embodiments, the duty cycle of the heater wire 315 may be set between and including approximately 80% to approximately 100% when the wire 315 is used to power an oxygen sensor. Thus, the duty cycle can be increased to a value higher than values in this range, including, as one example, a 100% duty cycle, which may provide a 12 volt power supply to the signal conditioning module 210. In some embodiments, the ECU 115 sets the duty cycle of the heater wire 315. In other embodiments, the signal conditioning module 210 sets the duty cycle of the positive heater wire 315. By receiving power through the positive heater wire 315 (previously used to provide power to a heating element of a narrow-band oxygen sensor 105A, 105B), the signal conditioning module 210 does not require an independent power coupling nor a new electrical harness, which reduces the cost and complexity of installing the signal conditioning module 210 and the associated wide-band oxygen sensors 205A, 205B. The lack of an independent power coupling improves serviceability and supports the addition of accessories by not utilizing a service or communication port or an accessory power port available on some vehicles.

The wide-band oxygen sensors 205A, 205B consumes current (pumping current) proportional to the air-to-fuel ratio. Thus, the signal conditioning module 210 measures the pumping current consumed by the wide-band oxygen sensors 205A, 205B (first data) via the sensor signal wire 405 of the second electrical couplings 220A, 220B. In one embodiment, the pumping current consumed by the wide-band oxygen sensors 205A, 205B are decimal representations of the air-to-fuel ratio of the engine.

The signal conditioning module 210 converts the measured pumping currents consumed by the wide-band oxygen sensors 205a, 205B (the first data) into a format (for example, a voltage range) acceptable by the ECU 115 (second data). The signal conditioning module 210 outputs the converted output voltages (the second data) to the electrical harness 110 via the sensor signal wire 305 of the first electrical couplings 215A, 215B. In some embodiments, the signal conditioning module 210 is configured to output other data to the ECU 115 via the electrical harness 110 in addition to data representing an air-to-fuel ratio. For example, when the signal conditioning module 210 does not receive an output from one or both of the wide-band oxygen sensors 205A, 205B, the signal conditioning module 210 may be configured to transmit a signal having a predetermined voltage or range (for example, at least a 4.5 volt signal) via the first electrical coupling 215A, 215B to the electrical harness 110 to notify the ECU 115 of a potential failure or malfunction (collectively referred to herein as a "fault") of a wide-band oxygen sensor 205A, 205B, the electrical harness 110, an electrical coupling 215A, 215B, 220A, or 220B, or a combination thereof.

The electrical harness 110 forwards the received converted output voltages to the ECU 115 via the coupling 130, which is the same coupling the electrical harness 110 uses when narrow-band oxygen sensors 105A, 105B are included in the system 100. By providing the converted output voltages to the ECU 115 through the electrical harness 110, the signal conditioning module 210 does not require an independent coupling to the ECU 115 nor does the system 100 require a new ECU, which reduces the cost and complexity of installing the signal conditioning module 210 and the associated wide-band oxygen sensors 205A, 205B. For example, in some embodiments, the ECU 115 used with the narrow-band oxygen sensors 105A, 105B is reused with the wide-band oxygen sensors 205A, 205B but is reflashed to process the converted output voltages provided by the signal conditioning module 210.

Thus, embodiments described herein provide a signal conditioning module for a wide-band oxygen sensor and a method of installing the same. By using existing electronic hardware and couplings, the signal conditioning module is easy to install. Although the above description relates to replacing existing narrow-band oxygen sensors with wide-band oxygen sensors, the signal conditioning module and method of installation described above is equally useful as part of an original installation in a vehicle. For example, using an existing electrical harness and ECU with the above-described signal conditioning module eliminates the need to re-design and re-tool an electrical harness, an ECU, or both. Accordingly, in these embodiments, the signal conditioning module can be installed as described above without the need to initially decouple one or more existing narrow-band oxygen sensors or the need to reprogram an existing ECU.

Various features and advantages of the invention are set forth in the following claims.

What is claimed is:

1. A signal conditioning module for a wide-band oxygen sensor installed in a vehicle, the signal conditioning module comprising:
   an electronic processor;
   a first electrical coupling configured to be coupled to a port of an electrical harness, the port configured to receive an electrical coupling of a narrow-band oxygen sensor for providing power to the narrow-band oxygen sensor, and
   a second electrical coupling configured to be coupled to the wide-band oxygen sensor, wherein the electronic processor receives power over the first electrical coupling, powers the wide-band oxygen sensor over the second electrical coupling using the power received over the first electrical coupling, receives first data over the second electrical coupling from the wide-band oxygen sensor, converts the first data to second data, and outputs the second data over the first electrical coupling to the electrical harness for transmission to an electronic control unit coupled to the electrical harness.

2. The signal conditioning module of claim 1, wherein the first electrical coupling includes a sensor signal wire, a signal ground wire, a heater wire, and a heater ground wire.

3. The signal conditioning module of claim 2, wherein a duty cycle of the heater wire is increased from a first level for powering the narrow-band oxygen sensor to a second level for powering the signal conditioning module.

4. The signal conditioning module of claim 1, wherein the second electrical coupling includes two sensor signal wires, a signal ground wire, a positive heater wire, and a negative heater wire.

5. The signal conditioning module of claim 1, wherein the first data is a pumping current consumed by the wide-band oxygen sensor.

6. The signal conditioning module of claim 1, wherein the second data is a voltage.

7. The signal conditioning module of claim 1, wherein the signal conditioning module is further configured to output a signal with a predetermined voltage to the electrical harness via the first electrical coupling when a fault is detected of at least one selected from a group consisting of the wide-band oxygen sensor, the electrical harness, the first electrical coupling, and the second electrical coupling.

8. The signal conditioning module of claim 7, wherein the predetermined voltage is at least 4.5 volts.

9. A method of installing a signal conditioning module for a wide-band oxygen sensor, the method comprising:
coupling a first electrical coupling of the signal conditioning module to a port of an electrical harness configured to be coupled to a narrow-band oxygen sensor; and
coupling a second electrical coupling of the signal conditioning module to the wide-band oxygen sensor,
the signal conditioning module receiving power over the first electrical coupling, powering the wide-band oxygen sensor over the second electrical coupling using power received over the first electrical coupling, receiving first data over the second electrical coupling from the wide-band oxygen sensor, converting the first data to second data, and outputting the second data over the first electrical coupling to the electrical harness for transmission to an electronic control unit coupled to the electrical harness.

10. The method of claim 9, further comprising uncoupling the narrow-band oxygen sensor from the port of the electrical harness.

11. The method of claim 9, further comprising increasing a duty cycle of a heater wire included in the first electrical coupling from a first level for powering the narrow-band oxygen sensor.

12. A system for installing a wide-band oxygen sensor in a vehicle, the system comprising:
the wide-band oxygen sensor;
an electrical harness, the electrical harness coupled to a power source included in the vehicle and including a port configured to be coupled to a narrow-band oxygen sensor for providing power to the narrow-band oxygen sensor and receiving data from the narrow-band oxygen sensor; and
a signal conditioning module, the signal conditioning module including a first electrical coupling configured to be coupled to the port of the electrical harness and a second electrical coupling configured to be coupled to the wide-band oxygen sensor,
wherein the signal conditioning module receives power over the first electrical coupling, powers the wide-band oxygen sensor over the second electrical coupling using the power received over the first electrical coupling, receives first data over the second electrical coupling from the wide-band oxygen sensor, converts the first data to second data, and outputs the second data over the first electrical coupling to the electrical harness for transmission to an electronic control unit coupled to the electrical harness.

13. The system of claim 12, wherein the first electrical coupling includes a sensor signal wire, a signal ground wire, a heater wire, and a heater ground wire.

14. The system of claim 13, wherein a duty cycle of the heater wire is increased from a first level for powering the narrow-band oxygen sensor to a second level for powering the signal conditioning module.

15. The system of claim 12, wherein the second electrical coupling comprises two sensor signal wires, a signal ground wire, a positive heater wire, and a negative heater wire.

16. The system of claim 12, wherein the first data is a pumping current consumed by the wide-band oxygen sensor.

17. The system of claim 12, wherein the second data is a voltage.

18. The system of claim 12, wherein the signal conditioning module is further configured to output a signal with a predetermined voltage to the electrical harness via the first electrical coupling when a fault is detected of at least one selected from a group consisting of the wide-band oxygen sensor, the electrical harness, the first electrical coupling, and the second electrical coupling.

19. The system of claim 18, wherein the predetermined voltage is at least 4.5 volts.

* * * * *